United States Patent

Burgess, Jr. et al.

[11] Patent Number: 5,082,629
[45] Date of Patent: Jan. 21, 1992

[54] THIN-FILM SPECTROSCOPIC SENSOR

[75] Inventors: Lloyd W. Burgess, Jr., Seattle; Don S. Goldman, Richland, both of Wash.

[73] Assignees: The Board of the University of Washington, Seattle; Battelle Development Corporation, Richland, both of Wash.

[21] Appl. No.: 459,078

[22] Filed: Dec. 29, 1989

[51] Int. Cl.$^5$ .............................................. G01N 21/00
[52] U.S. Cl. ................. 422/82.11; 422/82.05; 356/128; 385/12; 385/37
[58] Field of Search .................. 422/82.11, 82.05; 250/227.14; 350/96.1, 96.30; 356/128

[56] References Cited

U.S. PATENT DOCUMENTS

| | | | |
|---|---|---|---|
| 3,177,759 | 4/1965 | Wilks, Jr. | 356/51 |
| 3,242,805 | 3/1966 | Harrick | 350/355 |
| 3,308,709 | 3/1967 | Harrick | 350/96.1 |
| 3,433,570 | 3/1969 | Hansen | 356/128 |
| 3,436,159 | 4/1969 | Harrick et al. | 356/256 |
| 3,501,241 | 3/1970 | Hansen et al. | 356/244 |
| 3,604,927 | 9/1971 | Hirschfeld | 250/483.1 |
| 3,669,545 | 6/1972 | Gilby | 356/320 |
| 3,822,928 | 7/1974 | Smolinsky et al. | 350/96.12 |
| 3,996,576 | 12/1976 | Bullock | 356/10 |
| 3,998,591 | 12/1976 | Eckfeldt | 422/82.11 |
| 4,201,222 | 5/1980 | Haase | 128/634 |
| 4,213,462 | 7/1980 | Sato | 128/634 |
| 4,228,192 | 10/1980 | Sanden | 422/82.11 |
| 4,399,099 | 8/1983 | Buckles | 422/58 |
| 4,436,420 | 3/1984 | Depp et al. | 356/128 |
| 4,531,809 | 7/1985 | Carter et al. | 350/96.19 |
| 4,595,833 | 6/1986 | Sting | 250/353 |
| 4,608,344 | 8/1986 | Carter et al. | 431/34 |
| 4,637,684 | 1/1987 | Tomita et al. | 350/96.19 |
| 4,640,574 | 2/1987 | Unger | 350/96.19 |
| 4,661,320 | 4/1987 | Ito et al. | 422/86 |
| 4,671,938 | 6/1987 | Cook | 422/57 |
| 4,691,982 | 9/1987 | Nishimura et al. | 350/96.12 |
| 4,705,346 | 11/1987 | Miyawaki | 350/96.13 |
| 4,706,677 | 11/1987 | Goorsky et al. | 128/634 |
| 4,718,417 | 1/1988 | Kitrell et al. | 607/7 |
| 4,730,882 | 3/1988 | Messerschmidt | 350/96.1 |
| 4,746,179 | 5/1988 | Dahne et al. | 350/96.1 |
| 4,776,661 | 10/1988 | Handa | 350/96.19 |
| 4,787,690 | 11/1988 | Maerz | 350/96.12 |
| 4,800,886 | 1/1989 | Nestor | 128/634 |
| 4,815,843 | 3/1989 | Tiefenthaler et al. | 356/128 |
| 4,818,710 | 4/1989 | Sutherland et al. | 436/527 |
| 4,842,783 | 6/1989 | Blaylock | 264/1.4 |
| 4,877,747 | 10/1989 | Stewart | 422/58 |

FOREIGN PATENT DOCUMENTS 0254921 2/1988 European Pat. Off. ........... 350/96.1

OTHER PUBLICATIONS

Moshrezadeh et al., "Efficient Grating Couplers for Polymer Wageguides," *Appl. Opt.* 26:2501, 1987.

Tiefenthaler and Lukosz, "Sensitivity of Grating Couplers as Integrated-Optical Chemical Sensors," *J. Opt. Soc. Am. B* 6(2):209–220, 1989.

Lukosz and Tiefenthaler, "Integrated Optical Input Grating Couplers as Biochemical Sensors," *Sensors and Actuators* 15:285–295, 1988.

Lukosz and Tiefenthaler, "Sensitiveity of Integrated Optical Grating and Prism Couplers as (Bio)Chemical Sensors," *Sensors and Actuators* 15:273–284, 1988.

Primary Examiner—Robert J. Warden
Assistant Examiner—Laura E. Collins
Attorney, Agent, or Firm—Seed and Berry (List continued on next page.)

[57] ABSTRACT

There is disclosed an integrated spectrometer for chemical analysis by evanescent electromagnetic radiation absorption in a reaction volume. The spectrometer comprises a noninteractive waveguide, a substrate, an entrance grating and an exit grating, an electromagnetic radiation source, and an electromagnetic radiation sensing device. There is further disclosed a chemical sensor to determine the pressure and concentration of a chemical species in a mixture comprising an interactive waveguide, a substrate, an entrance grating and an exit grating, an electromagnetic radiation source, and an electromagnetic radiation sensing device.

27 Claims, 4 Drawing Sheets

OTHER PUBLICATIONS

Tiefenthaler and Lukosz, "Embossing Technique for Fabricating Surface Relief Gratings on Hard Oxide Waveguides," *Applied Optics* 25(9):1499–1504, 1986.

Tiefenthaler and Lukosz, "Grating Couplers as Integrated Optical Humidity and Gas Sensors," *Thin Solid Films* 120:205–211, 1985.

Tiefenthaler and Lukosz, "Integrated Optical Switches and Gas Sensors," *Opt. Lett.* 10(4):137–139, 1984.

Lukosz and Tiefenthaler, "Embossing Technique for Fabricating Integrated Optical Components in Hard Inorganic Waveguiding Materials," *Opt. Lett.* 8(10):537–539, 1983.

Spohn and Seifert, "Interaction of Aqueous Solutions with Grating Couplers Used as Integrated Optical Sensors and Their pH Behaviour," *Sensors and Actuators* 15:309–324, 1988.

Hewak and Lit, "Fabrication of Tapers and Lenslike Waveguides by a Microcontrolled Dip Coating Procedure," *Applied Optics* 27(21):4562–4564, 1988.

THIN-FILM SPECTROSCOPIC SENSOR

TECHNICAL FIELD

This invention relates to an integrated spectrometer for chemical analysis in a reaction volume utilizing a waveguide for the spectral analysis of chemical species. The invention further relates to a chemical sensor to detect concentrations of particular chemical species.

BACKGROUND OF THE INVENTION

There is a continuing need for improved chemical sensing devices to be able to continuously and reliably measure a particular analyte or analytes in a process stream. Since the introduction of solid and gas lasers more than two decades ago, there has been interest in a class of optoelectronic devices that rely upon the use of a light beam in solids for their operation for chemical sensing. An example of a solid is an optical fiber. Typical devices falling within the scope of that class are optical modulators, frequency mixers, parametric oscillators, and the like. More recently, there has been interest in using integrated optics with the application of thin-film technology to optical circuits and devices. However, these devices are not generally used for chemical sensing.

Multiple internal reflectance has been used as a means to produce an evanescent wave that can interact with an analyte or analytes in the reaction volume adjacent to a light-propagating element. The interaction of the analyte or analytes modulates the evanescent wave. This is a means for analyzing the presence and concentration of a particular analyte or analytes in the reaction volume. The light-propagating elements or crystals have been commercially available as large, self-supporting cylindrical rods, rectangular crystals, or prisms and sold as accessories for laboratory spectroscopic instruments.

These thick elements were generally designed for the fundamental vibrations of the substance that usually occur in the infrared. Thus the thickness of the element was designed to produce from about 1 to 10 bounces of light (assuming a ray-type propagation of electromagnetic radiation rather than by waveform) at the upper surface of the element. This low number of interactions (i.e., bounces) of light with the analyte or analytes in the reaction volume diminishes the sensitivity of the element to adequately measure the very intense fundamental vibrations. Thus, thicker, self-supporting elements may not have the sensitivity to analyze the weaker absorbing analytes, especially in the near-infrared spectral region where vibrational overtones and combination modes occur. The near-infrared region is an important spectral region because many optical fibers are available to transmit light energy in this spectral region and detector arrays are available for rapid analysis.

Thus there is a need in the art to make the elements thinner, thereby increasing the interaction of the propagating wave of electromagnetic radiation with the analyte or analytes in the reaction volume. Another problem with thinner elements is that they no longer are self-supporting, which diminishes or renders more difficult the ability to couple light into the elements. Thus there is a need in the art to be able to efficiently couple light into extremely thin elements, such as waveguides.

Planar waveguide technology began to be actively pursued in the 1960s in the semiconductor industry, with the goal of producing integrated optical circuits for microwave devices and networks. Much of the work for thin-film, planar waveguides and methods to couple light into them were also directed to these semiconductor industry objectives.

Much research has been directed toward the development of integrated optical components for semiconductor applications employing optical circuits. These devices typically employ thin-film dielectric or polymeric waveguides that are often less than 1 $\mu$m thick. This technology has advanced due to progress in the areas of photolithography, thin-film processing, and miniaturized laser light sources.

Optical propagation through a planar waveguide is described according to the following equations:

$$\text{(for } TE\text{)} \quad \tan^{-1}\frac{K_1}{n_2\cos X} + \tan^{-1}\frac{K_3}{n_2\cos X} + m\pi = ktn_2\cos X$$

$$\text{(for } TM\text{)} \quad \tan^{-1}\frac{n_2 K_1}{n_1^2\cos X} + \tan^{-1}\frac{n_2 K_3}{n_3^2\cos X} + m\pi = ktn_2\cos X$$

$$\text{where } K_i = \sqrt{n_2^2\sin^2 X - n_i^2} \text{ and } k = 2\pi/\lambda$$

wherein t is the film thickness; $n_i$ is the refractive index of the ith layer; and the subscripts 1, 2, and 3 refer to the sample, waveguide, and substrate, respectively. X is the angle in degrees between the axis of propagation of the optical mode (m) and the waveguide normal. Values of X can range between the critical angle $(\sin^{-1} n_3/n_2)$ to near 90°. A large value of X represents a mode that is traveling nearly parallel to the surface of the waveguide. TE represents a polarization in which the electric fields are perpendicular to the plane of incidence spanned by the wave normal and the normal to the interface. TM modes represent a polarization in which the magnetic fields are perpendicular to the plane of incidence.

A variety of thin films were examined for use as waveguide materials. Common waveguide materials include glasses; oxides, such as tantalum pentoxide; nitrides, such as silicon nitrate; and polymers, such as polystyrene and polycarbonate. A thin-film waveguide is characterized by a thin film with a higher refractive index than the materials (liquid or solid or gas) that bound its upper and lower surfaces. As a result, light or electromagnetic radiation can be focused through the materials surrounding the waveguide in a way that will cause light to be coupled into and propagated through the waveguide. What is required is a means to match the propagation constant for allowed waveguide propagation modes in order to couple externally generated light into the waveguide. Prism couplers had been used to accomplish this procedure.

The use of prisms to couple electromagnetic radiation into the waveguide has a number of disadvantages. The first disadvantage is the incompatibility of a prism structure with the overall planar geometry of a planar, thin-film waveguide. Second, the prisms must have a higher refractive index than the waveguide, which already may have a high refractive index (greater than 2.0). This limits the choice of prism materials. A third disadvantage is the need to maintain the coupling condition (have a constant space) between the prism and the waveguide material. Without the use of a bonding material, the prism often rests on small dust particles as it is clamped onto the waveguide. This makes it difficult to reproduce optical readings. Moreover, as a chemical sensor, the wicking of liquids or vapors into the volume between the prism and the waveguide poses problems for the performance of the optical sensor device by affecting the ability to reproducibly couple light into or out of the thin-film waveguide.

Some investigators have attempted to solve the third problem by attaching flow cells to a region on the waveguide and between the prisms and by not moving the prisms once they are clamped in place. See Ives et al., *Appl. Spect.* 68-72, 1988 and 41:636, 1988. However, this results in induced losses for the higher order modes passing under the gasket and causes cross-coupling between modes in multiple-moded waveguides. This may be adequate for research or laboratory applications but is not useful for field or commercial applications. Other approaches to solve the problem of light coupling into waveguides have used tapered ends to the waveguides or end couplers to "end fire" electromagnetic radiation in order to propagate through the waveguide.

Yet another approach has been the use of a grating on the upper surface of a thin-film, planar waveguide as a surface relief grating. Grating fabrication typically involves spin-casting a thin layer of a polymeric photoresist material, exposing the photoresist material to a desired pattern, and developing the exposed photoresist to leave the pattern on the waveguide film (*Dakss et al., App. Phy. Lett.* 16:523, 1970).

One problem has been that solvents and other chemicals used to fabricate gratings on polymeric waveguides may adversely affect the waveguide itself. Any chemical reaction with the grating material complicates signal analysis. Gratings have also been produced in the surface layer of inorganic waveguide materials by embossing the grating pattern in dip-coated gel films made from organometallic films before firing. This is referred to as a "surface relief grating." (See Lukosz et al., *Opt. Lett.* 8:537, 1983).

Moshrezadeh et al., *Appl. Opt.* 26:2501, 1987, refers to the use of a "buried" grating below the waveguide as an "incoupling grating" to characterize the nonlinear optical properties of the thin polymeric film.

U.S. Pat. No. 4,815,843 refers to the use of light fired into the waveguide from the substrate side, with buried gratings between the substrate and the waveguide. U.S. Pat. No. 4,815,843 refers to changes in measured signal due to changes in the refractive index induced by a chemisorbed layer formed over the grating from the reaction volume. Measurements are made by a change in angle with a rigid oxide waveguide between a conochromatic light source and an input grating at a fixed angle detector. This reference does not couple light into the waveguide from the substrate side. Other papers by Tiefenthaler refer to the same adsorptive effect using surface relief, embossed gratings rather than buried gratings.

Accordingly, there is a need in the art to design a planar, thin-film spectroscopic sensor that emphasizes sample spectral absorption rather than having the electromagnetic radiation coupling affected by adsorption from the reaction volume and can couple electromagnetic radiation into a thin-film waveguide without end-firing into too thick a material.

SUMMARY OF THE INVENTION

The present invention is able to create a sensitive chemical sensor by coupling electromagnetic radiation into and out of a thin-film waveguide, wherein the coupling gratings are buried at the waveguide/substrate interface. The multiple wavelength, miniaturized spectrometer has buried gratings at the waveguide/substrate interface under a thin-film waveguide to obtain evanescent absorption (i.e., internal reflectance) of electromagnetic radiation for liquids, gases, solids, or mixtures during continuous chemical analysis in a reaction volume. The integrated spectrometer may further function in a Raman or fluorescence mode based upon the absorption and emittance of electromagnetic radiation caused by the analyte or analytes in the reaction volume along the entire path of the thin-film waveguide between the gratings. Preferably, the waveguide has a planar geometry; however, the waveguide may have a current configuration. The waveguide is characterized by having a uniform thickness.

In one approach, the integrated spectrometer uses convergent, multiwavelength electromagnetic radiation e.g., "white light") that enters the waveguide from an incoupling or entrance grating. This causes each wavelength of electromagnetic radiation to be coupled into the waveguide at a unique angle, to propagate through the waveguide, and to exit the waveguide at an outcoupling grating at a unique angle. The complete spectral information leaving the waveguide at the outcoupling grating is obtained by placing a sensing device, such as a linear detector array, below the substrate and under the outcoupling grating or by transmitting the electromagnetic radiation exiting the waveguide to the sensing device with a fiberoptic lens or similar device.

The integrated spectrometer functions because every time a propagated beam of electromagnetic radiation bounces off the upper surface or first surface of the waveguide (that is in contact with the reaction volume), some of the power of the electromagnetic radiation is coupled into the reaction volume and absorbed by the analyte or analytes. The absorption is based upon the absorption characteristics of the analyte or analytes at each wavelength. The interactions of propagated light are integrated along the length of the waveguide, and the result is an absorption spectra of the analyte or analytes in the reaction volume that is similar to a standard transmission spectrum. This is called the "principle of attenuated total internal reflectance." Attenuated total internal reflectance is particularly suited to the analysis of mixtures that scatter light and are thus not readily amenable for transmission analysis, such as with a flow cell with optical windows. Thus, the sensitivity of the integrated spectrometer is proportional to the number of reflections that occur along the waveguide. Accordingly, one can increase the sensitivity of the integrated spectrometer by decreasing the thickness of the waveguide to increase the number of internal reflections.

The waveguide can have control over the mode structure due to its physical dimensions and material properties. The selection of the material is further determined by the particular wavelengths of light (electromagnetic radiation) needed to propagate through the waveguide. If the waveguide is sufficiently thick to support several modes, then different modes can be selected for more or less evanescent penetration into the reaction volume at each wavelength. The number of modes is determined by waveguide thickness and the refractive indices of the waveguide, sample, and substrate. Moreover, the angle required to couple light into a mode for a particular waveguide decreases as the wavelength of the light increases.

One aspect of the present invention is an integrated spectrometer for liquid, gas or solid phase chemical analysis. A second aspect of the present invention is a chemical sensor to sense the presence of a particular vapor or solvent. The spectrometer and the sensor measure chemical species based upon different principles. The spectrometer relies upon evanescent absorption using a waveguide material that does not interact, that is, change its physical properties when in contact with the sample in the reaction volume. Multiple wavelengths of electromagnetic radiation will most often be used in the spectrometer. The chemical sensor will use a waveguide material that interacts with and physically changes in the presence of a particular solvent, solvents, or vapor in the reaction volume. Thus, the physical thickness and/or refractive index of the chemical sensor waveguide change in response to the incorporation of the particular vapor, solvent, or solvents. The physical change in the waveguide modulates the propagation of electromagnetic radiation and thus the signal from the sensor. Preferably, the chemical sensor uses a single wavelength of electromagnetic radiation.

The integrated spectrometer and the chemical sensor comprise a thin-film, planar waveguide, a substrate, an electromagnetic radiation source, and an electromagnetic radiation sensing device. The waveguide has a uniform thickness and a first surface and a second surface, wherein the first surface communicates with the reaction volume and the second surface communicates with the gratings and the substrate. The waveguide of the integrated spectrometer is noninteractive and does not physically change or change its refractive index when in contact with a reaction volume. The waveguide of the chemical sensor has an additional feature of waveguide dynamics when in contact with the particular vapor or solvent. This means that the waveguide is interactive and changes its refractive index and/or thickness.

The substrate has a top surface and a bottom surface and comprises a material that allows for the transmission of electromagnetic radiation. The substrate further comprises an entrance or incoupling grating and an exit or outcoupling grating etched or deposited on the top surface of the substrate. The entrance grating communicates with the entrance end and the second surface of the waveguide and couples electromagnetic radiation into the waveguide. The exit grating or outcoupling grating communicates with the exit end and the second surface of the waveguide and couples electromagnetic radiation out of the waveguide. In the basic configuration, the gratings comprise parallel lines with constant spacings that diffract electromagnetic radiation of particular wavelengths to match the conditions for light propagation in the waveguide in the region between the gratings. More complicated grating structures can be utilized to further facilitate the incoupling and outcoupling of multiple wavelength light. For example, a "chirped" grating has variable spacings between the grooves. More particularly, a chirped grating permits collimated white light to be used rather than convergent white light. Curved grating can help focus electromagnetic radiation into the waveguide.

The electromagnetic radiation source is directed toward the entrance grating. The spectrometer (e.g., linear array detector) or electromagnetic radiation sensing device is directed toward the exit grating. Preferably, the device has a means for directing electromagnetic radiation between the entrance grating and the electromagnetic radiation source and between the exit grating and the sensing device. The means for directing can be, for example, a fiber optic to transport light and/or a lens to focus light.

The integrated spectrometer can further comprise a polymeric overcoat layer communicating with the first surface of the waveguide. The overcoat layer is thinner than the waveguide or wavelength of electromagnetic radiation and permits evanescent interaction of the electromagnetic radiation with the reaction volume. The overcoat may be used to protect the first surface of the waveguide from chemical alteration or to alter the waveguide surface energy. However, the overcoat must be thin enough in the region between the gratings to allow evanescent absorption from the reaction volume.

The waveguide is usually composed of metal oxide, a nitride, a glass, or a polymeric material. It is possible that the waveguide may be permeated by or swell when put in contact with a particular reaction volume containing a vapor or solvent. The chemical sensor waveguide is preferably a polymeric material capable of being permeated or swelled. As the waveguide changes thickness or refractive index, this causes the angle required to couple electromagnetic radiation (via a grating) into the waveguide to change at a particular wavelength. This change in the physical parameters of the waveguide changes coupling conditions for light fired into the waveguide and outcoupled from the waveguide. The effect for a given waveguide/sample interaction may be quantified to measure the concentration of the vapor or solvent (i.e., chemical species).

Each wavelength of electromagnetic radiation has a specific angle required to enter the waveguide and propagate through the waveguide. As the wavelength of the electromagnetic radiation increases, for a fixed waveguide thickness (e.g., noninteractive waveguide), the angle at which electromagnetic radiation of that waveguide couples into the waveguide decreases, and vice versa. The grating, acting like an internal prism, changes the direction of electromagnetic radiation based upon its wavelength, the grating period (spacing), the diffraction order, and the refractive indices of the surrounding materials (substrate and waveguide). Thus, a particular angle must be used to enter a fixed period grating from the substrate for each wavelength. The grating will alter that angle and enable electromagnetic radiation of the particular wavelength to couple into the waveguide. For a multiple-mode waveguide, a particular wavelength will couple into the different modes at different angles. Thus, the theory for waveguide propagation is combined with a theory for gratings to form this miniaturized spectrometer.

BRIEF DESCRIPTION OF THE DRAWINGS

FIG. 2 shows the relationship between the angle of light entering the lower side of the substrate (as measured from the substrate to normal) with the resulting wavelength that that angle will accept. FIG. 2 shows that, for this particular waveguide, substrate grating, and reaction volume, white light entering the grating at normal incidence (0°) will exit at the outcoupling grating at (0 ) normal incidence as 0.9-μm light.

FIG. 3 shows the result of permeation of the polymer waveguide by an organic vapor. The vertical line in FIG. 3 represents the coupling conditions for a 0.3-μm thick polystyrene waveguide at a wavelength of 0.63 μm corresponding to a HeNe laser. Under these conditions, only one mode was available, which will propagate at an angle to the waveguide of about 69.5°. Each line is a separate mode propagated through the planar waveguide. FIG. 3 shows that the angle required to couple light into each mode is dependent upon the wavelength of light and the thickness of the waveguide at a given waveguide refractive index. If the thickness of the waveguide increases, the vertical line in FIG. 3 shifts to the right and a new (greater) angle is required for coupling. Signal attenuation results as this new required angle deviates from the initial coupling configuration. The results in FIG. 4 show this effect. It is noted that a change in the waveguide refractive index due to solvent permeation can also cause such a change.

The buried grating located between the substrate and the waveguide is used to diffract light into the desired waveguide mode from the substrate. The equation for the grating is:

$$d(n_2 sinX - n_3 sin\phi) = p\lambda$$

wherein d is the grating spacing, p is the diffraction order, and $\phi$ is the angle incident on the grating in the substrate. The angle of interest is $\Omega$, which is located at the back surface of the substrate between the light beam and substrate normal.

Snell's law is:

$$sin\Omega = n_3 sin\phi$$

Thus, the grating equation can be rewritten as:

$$sin\Omega = n_2 sinX - p\lambda/d$$

This allows the mode equation to be solved numerically for a given sample/waveguide/substrate configuration and to determine the angle of propagation within the waveguide. This waveguide angle (X) can be related to the angle external to the substrate ($\Omega$) by the grating equation for a given grating configuration.

Figure 4:
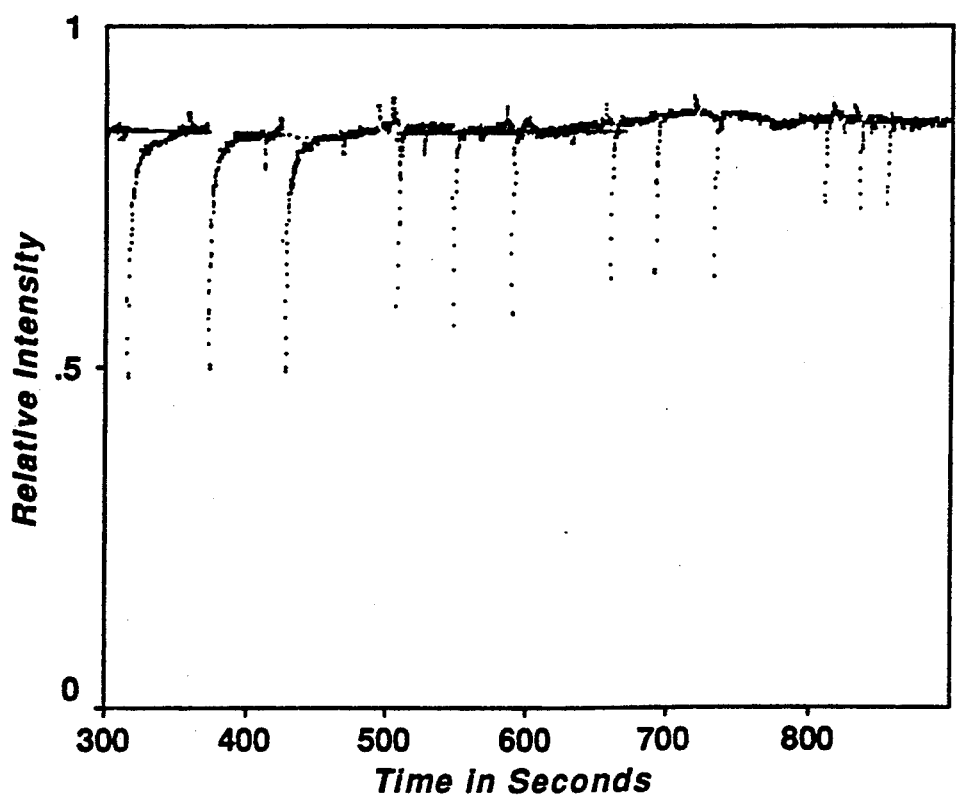

FIG. 4 shows a signal attenuating pattern of the chemical sensor described in Example 5. The chemical sensor responds to pentane vapor, which was applied over several concentrations, three times at each concentration. The comparisons of each of the triplicates show the signal intensity as a function of relative pentane vapor concentration.

Figure 5:
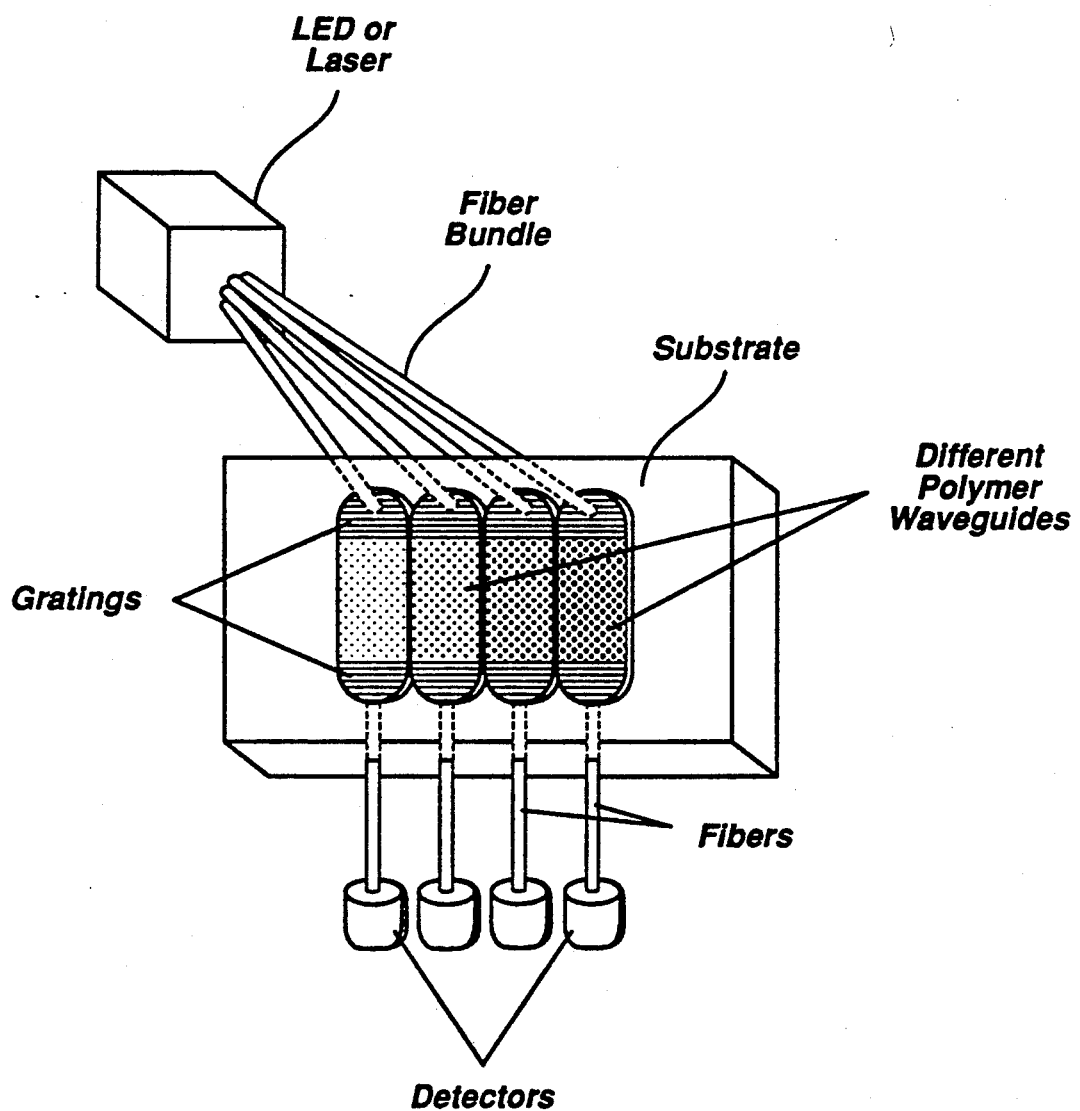

FIG. 5 illustrates the use of monochromatic light with several grating pairs. Each pair is covered by a different polymeric planar waveguide on the same substrate. This planar waveguide array can be used as a vapor mixture analyzer. The source of electromagnetic radiation is a laser (10) connected, via a fiber bundle, into an entrance grating for each different polymer waveguide.

Figure 6:
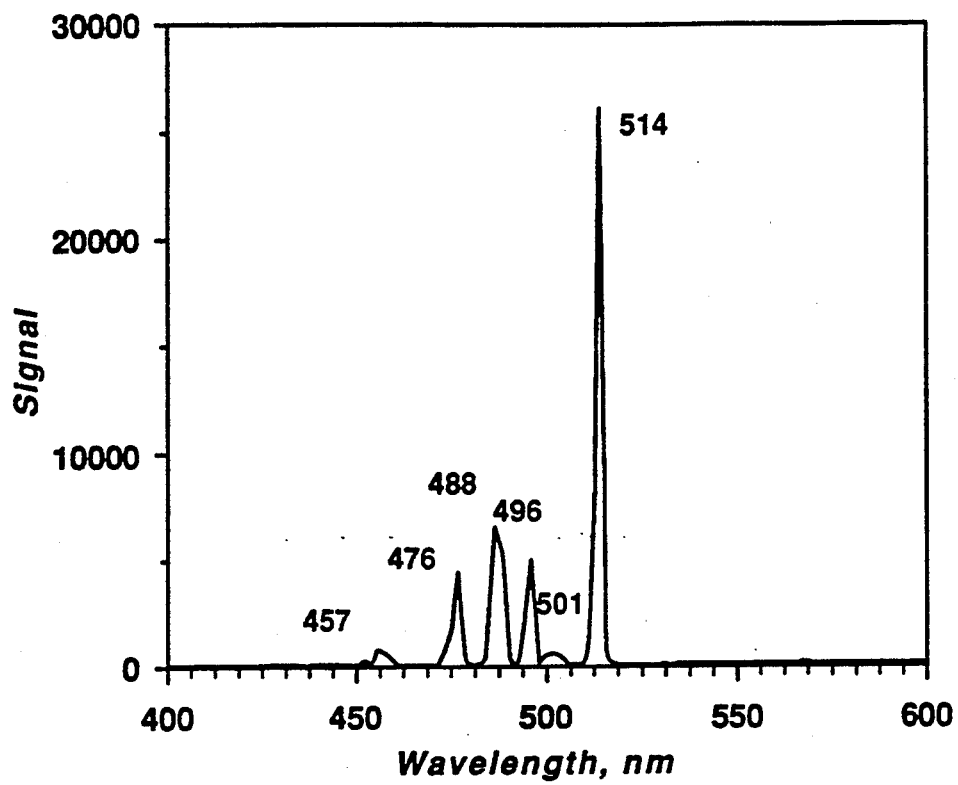

FIG. 6 shows the spectrum of light from an argon laser operated in a multiple mode that was used as the source signal for an incoupling grating of a 0.42 μm thick polystyrene waveguide on a glass substrate having 0.4 μm period gratings.

Figure 7:
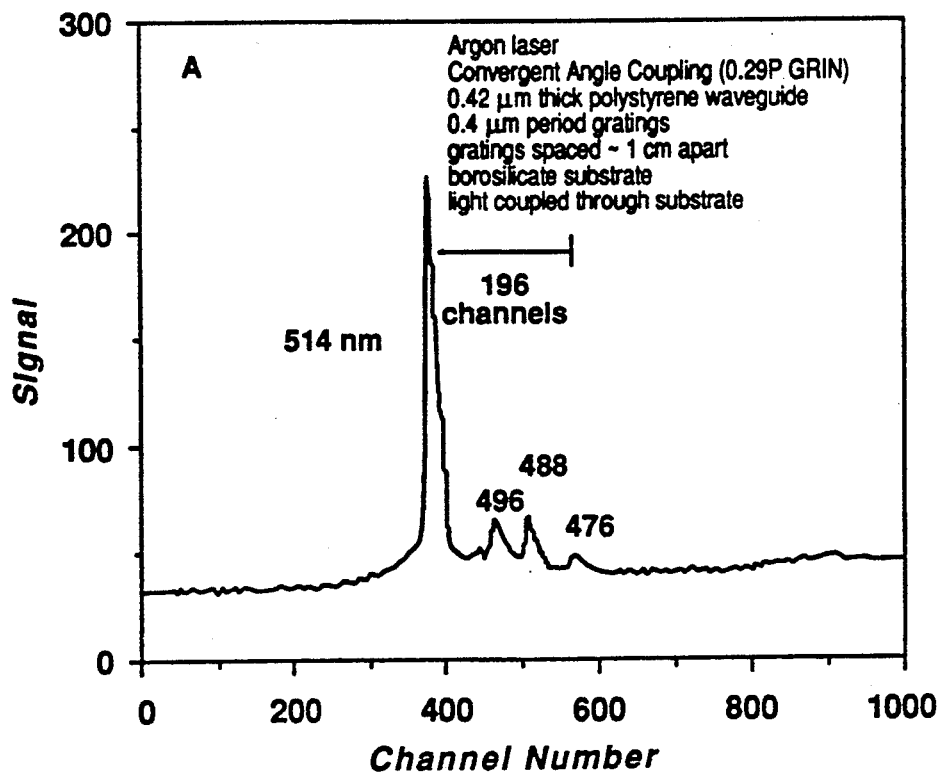

FIG. 7 shows the outcoupled signal from a linear array detector measuring the spatially dispersed light from the arrangement in FIG. 6. The array channel numbers are assigned to each element of the array. FIG. 7 shows that the outcoupling grating disperses each wavelength of light at a different angle. Each angle, in turn, is incident upon a different element in the array.

DETAILED DESCRIPTION OF THE INVENTION

The present invention comprises an integrated spectrometer for chemical analysis by evanescent electromagnetic radiation absorption in a reaction volume. The inventive device comprises a waveguide, a substrate, an entrance grating and an exit grating, an electromagnetic radiation source, and a sensing device for the electromagnetic radiation.

The present invention further includes a method for continuously measuring the concentration of an analyte or analytes in a reaction volume and a method of sensing a concentration of a vapor or solvent in a reaction volume by a chemical sensor. The inventive method comprises contacting a first surface of a waveguide, having a uniform thickness, with a reaction volume. The waveguide further comprises a second surface communicating with an analysis device. The analysis device comprises a substrate having a top surface communicating with a second surface of the waveguide, and a bottom surface, wherein the substrate consists of a material characterized by allowing for the transmission of the appropriate wavelengths of electromagnetic radiation and by having a different refractive index from the waveguide. The substrate further comprises entrance and exit gratings etched into or deposited on the top surface of the substrate such that the entrance grating couples electromagnetic radiation into the waveguide and the exit grating couples electromagnetic radiation out of the waveguide.

The analysis device further comprises an electromagnetic radiation source directed toward the entrance grating and an electromagnetic radiation sensing device directed toward the exit grating. Preferably, the device further comprises a means to transmit the electromagnetic radiation from the source to the entrance grating and from the exit grating to the sensing device.

After contacting the first surface of a waveguide with the reaction volume, the method directs electromagnetic radiation to propagate through the waveguide such that the interaction of the analyte or analytes along the first surface of the waveguide, between the gratings, modulates an electromagnetic radiation wave propagating through the waveguide. The inventive method then comprises detecting the wavelength and intensity of the electromagnetic radiation by the electromagnetic radiation sensing device. The interaction of the waveguide and the reaction volume occurs by one of two procedures. With a noninteractive waveguide, the evanescent wave will penetrate into the reaction volume for absorption by the analyte or analytes. The intensity loss of a particular wavelength or mode of light will be measured and directly correlated to the concentration of analyte or analytes with an interaction waveguide. Preferably, single wavelength light is used for the interactive waveguide. The measurement of a chemical species such as a solvent or vapor, in a mixture is acccomplished by having the refractive index of the waveguide change in the presence of the chemical species or by a physical change in the thickness of the waveguide. These changes (thickness and refractive index) will most likely occur simultaneously. The refractive index can change in response to a physical change in the waveguide, such as a thickness change or a filling of the pores.

The thin-film, planar waveguide is supported on a substrate. The substrate is characterized by allowing for transmission of the electromagnetic radiation through the substrate. Examples of substrate materials include glass, fused silica, and sapphire for ultraviolet, visible, and near-infrared wavelengths; materials such as zinc selenide for infrared wavelengths; and calcium fluoride for near-infrared and infrared wavelengths. It is important that the substrate allow for transmission of the particular wavelengths of interest of electromagnetic radiation, have low surface roughness, and have a different refractive index than the waveguide.

The gratings are "buried" beneath the waveguide on the top surface of the substrate. There is both an entrance (or incoupling) grating for incoupling of the particular wavelength(s) of electromagnetic radiation into the waveguide and an exit (or outcoupling) grating for outcoupling of the particular wavelength(s) of electromagnetic radiation out of the waveguide. The outcoupled electromagnetic radiation is directed toward the electromagnetic radiation sensing device located beneath the substrate. Therefore, the gratings function to couple the specific wavelengths of electromagnetic radiation, such as visible light, into and out of the waveguide without being in contact with the reaction volume.

The gratings can be of several types, such as etched or ruled onto the substrate surface. Further, the gratings can be an ultrathin metal grating located on the substrate surface and containing vapor-deposited, ultrathin, narrow metal lines separated by bare substrate. Other grating designs may more easily collimate and disperse the electromagnetic radiation and are often used for spectroscopic applications. These grating designs include chirped and curved gratings. Chirped gratings have a variable spacing between the grooves. The grating spacing largely controls the angle at which electromagnetic radiation, at a given wavelength and for a given set of waveguide, substrate, and boundary conditions, will couple into the waveguide. For example, a 0.5-$\mu$m grating spacing used for the calculation in FIG. 2 causes light (electromagnetic radiation) having a wavelength of about 1.2 $\mu$m to couple into that waveguide at $-60°$. (measured from the normal to the substrate). If the grating spacing was increased to 0.7 $\mu$m, slightly longer wavelength light of about 1.5 $\mu$m would be coupled into the waveguide at $-60°$. Minus angles describe an incoupling angle to the back of the substrate that point in a direction away from the outcouple gratings as measured from the normal to the back of the substrate (see FIG. 1). Conversely, smaller grating spacings shift the curve in FIG. 2 toward shorter wavelengths. This is the way by which the same waveguide material could be used to analyze different spectral regions (e.g., visible and near-infrared). The chirped grating allows collimated white light, impinging on a chirped grating, to be directed into the waveguide at a variety of angles.

The waveguide material is a noninteracting waveguide for the chemical spectrometer that is insensitive or static to its chemical environment. The use of noninteractive waveguides is for an integrated spectrometer for chemical analysis by evanescent electromagnetic radiation absorption. Examples of waveguide materials for noninteracting waveguides include glass; fused silica; metal oxides, such as $Ta_2O_5$, $ZrO_2$, $Al_2O_3$, and other oxides; nitrides, such as $Si_3N_4$; and noninteractive polymers. For infrared applications, it is possible to have a waveguide of a combination material of Si or Ge on a substrate with a lower refractive index (e.g., zinc selenide).

The preferred ratio of the waveguide thickness-to-depth-of-grating for etched gratings is from about 1:10 to about 5:1, and preferably about 2:1. However, the thickness to grating depth ratio is dependent upon the grating or waveguide fabrication methods. One would prefer to have deeper gratings to increase incoupling efficiency and thinner waveguides to have single mode behavior. For a tantalum pentoxide waveguide, a preferred ratio is about 2:1 or greater, e.g., about 0.2 $\mu$m thick or greater waveguide and 0.1 $\mu$m depth gratings when etched on glass.

For chemical sensor applications, the waveguide should be made from a material which will physically interact with its chemical environment. Examples of materials for use as a chemical sensor waveguide include polymeric materials, such as polystyrene, silicone, and polymethylmethacrylate.

Figure 1:
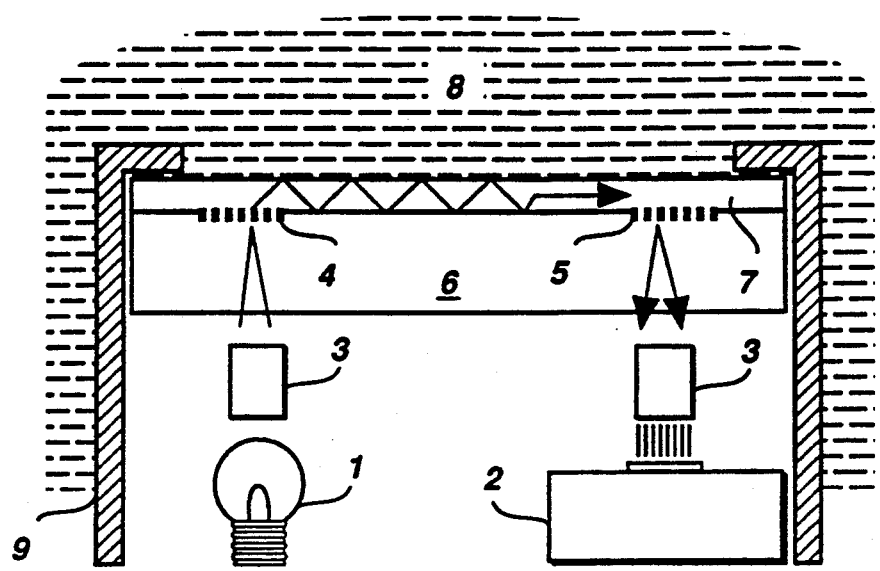
FIG. 1 is a schematic illustrating one embodiment of an integrated spectrometer or chemical sensor using the inventive device. The device comprises an electromagnetic radiation source, such as a mono- or polychromatic light source (1), a spectrometer or electromagnetic radiation sensing device such as a single wavelength detector or linear array detector for spectral acquisition (2), optical lenses and fibers (3) for focusing and light (e.g., electromagnetic radiation) transmission (3). There is an incoupling diffraction grating (4) buried under the waveguide to guide light into the specific optical propagation modes in the waveguide. There is a similar outcoupling defraction grating (5) buried under the waveguide to guide light from the waveguide to the detector. A substrate (6) is compatible with the waveguide material and allows for transmission of the appropriate wavelengths of light. The waveguide (7) is in contact with the reaction volume (8). The location of the gratings buried beneath the waveguide allows the reaction volume to be separated from the light source and detection system when sealed in an enclosure (9), thereby making it useful for chemical monitoring.

The integrated spectrometer for liquid or gas chemical analysis by evanescent electromagnetic radiation absorption couples multiple-wavelength electromagnetic radiation incident on the entrance grating at a variety of angles into the waveguide. Preferably, the electromagnetic radiation is within the spectral range of ultraviolet light to near-infrared light. Most preferably, multiple-wavelength or single-wavelength visible light is used. The electromagnetic radiation sensing device is used to obtain spectroscopic data where the signal intensity of the light source varies as a function of wavelength. This can be achieved, for example, by the use of a broad-wavelength, visible light source (e.g., incandescent light bulb) and intervening collimating and condensing optics to focus the light on the entrance grating. This configuration is illustrated in FIG. 1 with a lens system (3) helping to focus the white light source (1) onto the entrance grating (4). The chemical sensor preferably uses single-wavelength light generated by a laser.

The integrated spectrometer can further comprise a reference waveguide in addition to the sample waveguide. The reference waveguide has an overcoat layer sufficiently thick to prevent evanescent interaction of the electromagnetic radiation propagating through the waveguide with the sample (analyte or analytes in the reaction volume). The overcoat layer coats at least the area between the gratings, and preferably the area over the gratings as well.

The reference waveguide and sample waveguide may be on the same substrate or different substrates. The sample waveguide does not have a thick overcoat layer. The electromagnetic radiation source of the reference waveguide may be shared with the sample waveguide in the same or different incoupling gratings. Similarly, the outcoupling gratings may be shared or separate to the same sensing device or separate sensing devices.

The use of a reference waveguide allows accounting for instrument variables, such as changes in the source intensity, in a similar fashion as dual-beam spectrometers.

Figure 2:
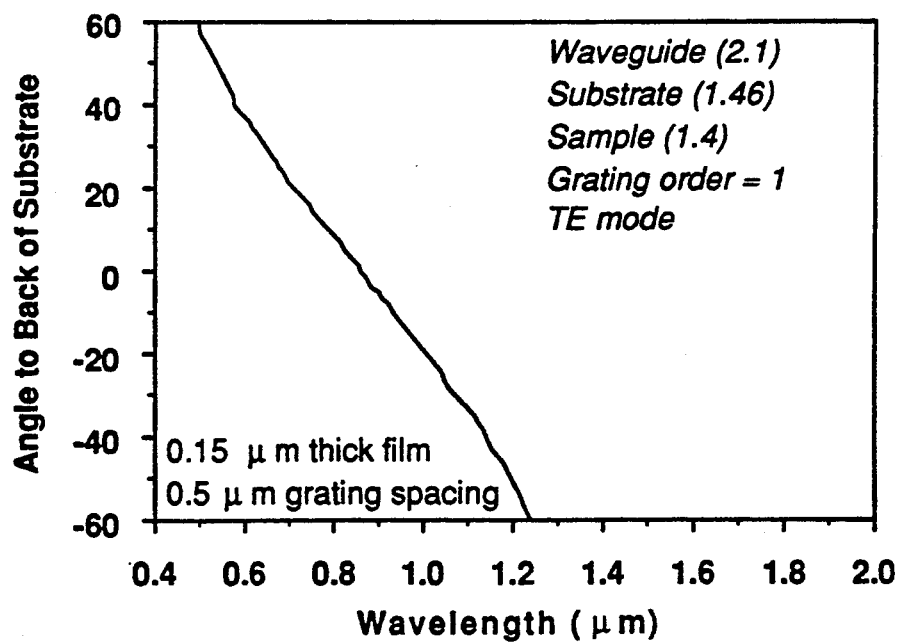
FIG. 2 illustrates the theory of waveguide propagation and gratings for an integrated spectrometer for near-visible and visible applications. The device used for the data in FIG. 2 consists of a $Ta_2O_5$ waveguide that is 0.15 μm thick on a fused silica substrate. The entrance and exit gratings had a constant spacing between the grooves of 0.5 μm. The waveguide was sufficiently thin in this configuration such that it only supported one optical mode. The compact spectrometer of FIG. 2 allows multiwavelength light to enter the waveguide at different angles simultaneously. The light is transmitted through the waveguide and dispersed at a characteristic angle for each wavelength, as shown in FIG. 2. Thus.

The integrated spectrometer for chemical analysis by evanescent electromagnetic radiation absorption is illustrated with the data shown in FIG. 2. FIG. 2 uses the integrated spectrometer configuration shown in FIG. 1. The integrated spectrometer used in FIG. 2 consists of a $Ta_2O_5$ material waveguide that is 0.15 $\mu$m thick on a fused silica substrate. Both the entrance and the exit gratings have a constant spacing between the grooves of 0.5 m. The gratings were fabricated using standard photolithography methods. The waveguide is sufficiently thin in FIG. 2 such that it supports only one optical mode. This integrated spectrometer design will work for visible light and near-visible light from approximately 0.4 $\mu$m to about 1.1 $\mu$m wavelengths. FIG. 2 shows that for each angle of white light entering the substrate (and by the law of refraction, entering the grating), the waveguide extracts a specific wavelength and transmits it through the waveguide. The specific wavelength of light propagates to the first surface of the waveguide many times so as to integrate the many evanescent penetrations into the reaction volume. The outcoupling grating (5) or exit grating outcouples the light from the waveguide so that the light is angularly dispersed according to wavelength. FIG. 1 has a collimating optic (3) that is preferably used to focus the light on a sensing device. Alternatively, the dispersed light exiting through the exit grating can be directed on a linear detector array so that each photosensitive element in the array samples a different wavelength of light or a narrow range of wavelengths of light. The interaction of the first surface of the waveguide with the reaction volume results in a characteristic spectrum which is a function of the presence and concentration of a specific analyte or analytes. Thus, spectral information can be obtained by extracting the electronic signals from the linear detector array with associated electronics and output devices.

The ultraviolet to near infrared region (up to 1.0 $\mu$m) is analyzed by commercially available silicon photodiode arrays (e.g., EG&G). The near-infrared region from 1.0 to 2.5 $\mu$m is analyzed by, for example, germanium (American Holographic) or indium gallium arsenide (Epitaxx).

Thicker waveguides support more propagation modes. The additional modes would appear similar to the curve shown in FIG. 2 but are displaced to the left. Thus, a thicker waveguide film will have several curves in a graph, such as shown in FIG. 2, with each curve corresponding to an additional mode. This means that, if collimated, white light (collimated through the use of a lens (3)) entered the waveguide at one angle, each mode would extract out a particular wavelength. Each wavelength would exit the waveguide at the outcoupling grating at an angle equivalent to the incoupling angle. Thus, a multiwavelength integrated spectrometer for chemical analysis by evanescent electromagnetic radiation absorption, based upon a thicker film, can contain a plurality of modes, each corresponding to the angle at which white light enters the waveguide from the incoupling grating. Thus, the spectral resolution will depend upon the number of modes and subsequent separation of each mode in a graph, such as the graph of FIG. 2.

Each mode interacts with the analyte or analytes in the reaction volume to a different degree. Thus the use of the two modes is equivalent to having two transmission cells of different lengths. The extraneous effects, such as changes in the waveguide surface or source signal strength, can be eliminated. This requires a separate analysis of each mode.

One way to resolve this situation is to induce a slight, permanent rotation in the direction of the outcoupling grating (5). The rotation would be different from the direction of the grooves of the incoupling grating (4). This would separate the different modes so that the outcoupling signals will be laterally separated, but each will contain spectral information for each mode as a function of angle, and will be projected below the outcoupling grating. Each signal would represent a different mode. Thus, a two-dimensional detector array (e.g., such as those used in video cameras) or a several parallel linear arrays could be used to analyze the different modes. This option permits the different sensitivities of the different modes to be simultaneously analyzed. This situation is also suited for reaction volumes containing the analyte or analytes having both weakly and strongly absorbing spectral regions.

The location of evanescent electromagnetic radiation absorption in the reaction volume occurs adjacent to the first surface of the waveguide in that region of the waveguide between the gratings. It is important that there be adequate distance between the gratings to allow for maximum sensitivity of the integrated spectrometer so as to allow a large enough region of interaction between the evanescent wave and the analyte or analytes in the reaction volume. For example, a 0.2-$\mu$m thick, single-moded waveguide ($Ta_2O_3$) may have about 4,000 to about 6,000 bounces against the first surface for gratings separated by a 1-cm distance. Therefore, although there can be interaction of the waveguide with the reaction volume above the gratings, it is the region of the waveguide between the gratings that is of interest for evanescent absorption of the electromagnetic radiation.

In many cases, the spectral information at one or only a few discreet wavelengths needs to be measured, rather than the complete spectrum of wavelengths that are emitted from a source of electromagnetic radiation. In other cases, it is necessary to have the sensing device or detector array be able to determine electromagnetic radiation of all of the particular wavelengths being used. For a single wavelength application, it is preferable to use a laser light source or a filtered, collimated white light source at a specific angle. A single detector, appropriately positioned, is adequate in this case. The single white light source at a wide range of angles, such as from +60 to −60. to the normal of the lower surface of the substrate, is illustrated in FIG. 2 using convergent white light. A linear detector array is used to analyze the light dispersed as a function of angle from the exit grating in this case. Similarly, single-element detectors can be placed at specific angles and focused toward the outcoupling grating in place of a linear detector array for the sensing device. This allows a particular wavelength to be picked up by, for example, a fiberoptic cable, and directed to the particular sensing device that can detect the electromagnetic radiation of a particular wavelength. Another approach is to use a series of apertures with the outcoupling optics (3) to improve the spectral resolution for each detector.

Alternatively, other grating designs may collimate and disperse the particular wavelengths of electromagnetic radiation. The other grating designs include chirped and curved gratings and a combined curved-chirped grating having the features of both types of gratings. Chirped gratings have a variable space in-between the grooves. A collimated format of multiple-band light will have a single incident angle to the grating. A regularly spaced grating will act as a filter to allow incoupling of only a single frequency. A chirped grating can allow the incoupling of a plurality of wavelengths. Thus, when using a collimated, white light, electromagnetic radiation source directed to a chirped incoupling grating, each wavelength of light will be directed into the waveguide at a different angle.

A chirped outcoupling grating will increase outcoupling efficiency by allowing multiple opportunities to outcouple a particular wavelength. A chirped outcoupling grating will further focus a particular wavelength of light to a particular point and another wavelength to an adjacent point.

Curved gratings will further assist with collimation. Curved gratings allow for focusing of light (electromagnetic radiation) at greater or lesser distances below the grating.

One problem using evanescent absorption from thin-film waveguides is that prolonged contact with a reaction volume may foul the first surface of the waveguide and seriously impair the usefulness of the spectroscopic device. There may also be a chemical attack of the waveguide material, depending on the nature of the chemistry in the reaction volume. The present invention further comprises an ultrathin (less than 0.01 μm) polymeric overcoat on the first surface of the waveguide. The polymeric overcoat layer is thinner than the evanescent penetration distance of the waveguide mode into the reaction volume. Preferably, this is about 10% of the wavelength. For example, the oxide-type waveguide materials used for the integrated spectrometer for chemical analysis have high-energy surfaces. An ultrathin polymeric overcoat layer could create a low energy, hydrophobic surface for oxide-type waveguide materials. Examples of polymers useful for polymeric overcoat layer materials include, for example, fluorocarbons or silanes.

The present invention further comprises a thicker overcoat layer. The thicker overcoating is placed over the gratings on the first surface of the waveguide. However, it is important that there be a noncoated distance between the gratings that does not have a thicker overcoat layer. The thick overcoat layer will prevent evanescent interaction of the waveguide with the reaction volume at sites other than between the gratings.

Alternatively, a thick overcoat layer can be applied over the first surface of the waveguide, including between the gratings. When this occurs, a first waveguide covered area is used as a reference beam in conjunction with a parallel sample, wherein the second waveguide does not have a thick overcoat layer between the gratings. The beam of electromagnetic radiation can be alternately switched between the overcoated and uncoated waveguides. Having both a sample and a reference beam can provide a ratio of intensities at the detector (2) for a self-referencing apparatus.

In another embodiment, the integrated spectrometer for chemical analysis can sense changes within an overcoat layer by evanescent penetration only within a thick overcoat layer located between the gratings. For example, if an acid-base indicator (e.g., Congo Red) that changes color as a function of pH is immobilized within the thick overcoat layer, such as a polymeric overcoat (e.g., cellulose, acetate) on an oxide-type waveguide (e.g., $Ta_2O_5$), changes in pH of the reaction volume will be reflected in a color change in the pH indicator in the thick overcoat layer. The change of color in the overcoat can be analyzed evanescently by the waveguide. In essence, the overcoat, modified by the analyte or analytes in the reaction volume, becomes the indicator for the waveguide. Thus, the integrated spectrometer with a thick overcoat layer can function as a pH measuring device, for example.

The present invention further comprises a chemical sensor to monitor for the presence or concentration of a particular chemical species (e.g., solvent or vapor) in a chemical composition, such as a mixture. The chemical sensor comprises a waveguide, preferably a polymeric waveguide, a substrate, an entrance grating, an exit grating, an electromagnetic radiation source, and an electromagnetic radiation sensing device. The waveguide has a uniform thickness, a first surface, and a second surface. The waveguide used for the chemical sensor is characterized as an interactive waveguide. This means that the waveguide structure will physically change as a result of interaction with the particular chemical species (e.g., particular solvent or vapor). The physical change results in an altered refractive index and/or thickness of the waveguide. The first surface of the waveguide communicates with reaction volume possibly containing the chemical species. For example, a waveguide composed of polystyrene will interact with acetone. Thus, the sensor will change to no signal where there was one, or signal when there was no signal after sufficient physical changes in the waveguide, such that no electromagnetic radiation of a particular wavelength can be propagated.

The substrate has a top surface and a bottom surface and comprises a material of a refractive index different from that of the waveguide. The substrate allows for the transmission of the appropriate wavelength of electromagnetic radiation. The top surface of the substrate supports the second surface of the waveguide and communicates with the waveguide. The entrance grating couples electromagnetic radiation into the waveguide and the exit grating couples electromagnetic radiation out of the waveguide. The electromagnetic radiation source is directed toward the entrance grating and the electromagnetic radiation sensing device is directed toward the exit grating. There may be further fiber optics to direct light between the source and the incoupling grating and between the outcoupling grating and the detector.

Figure 3:
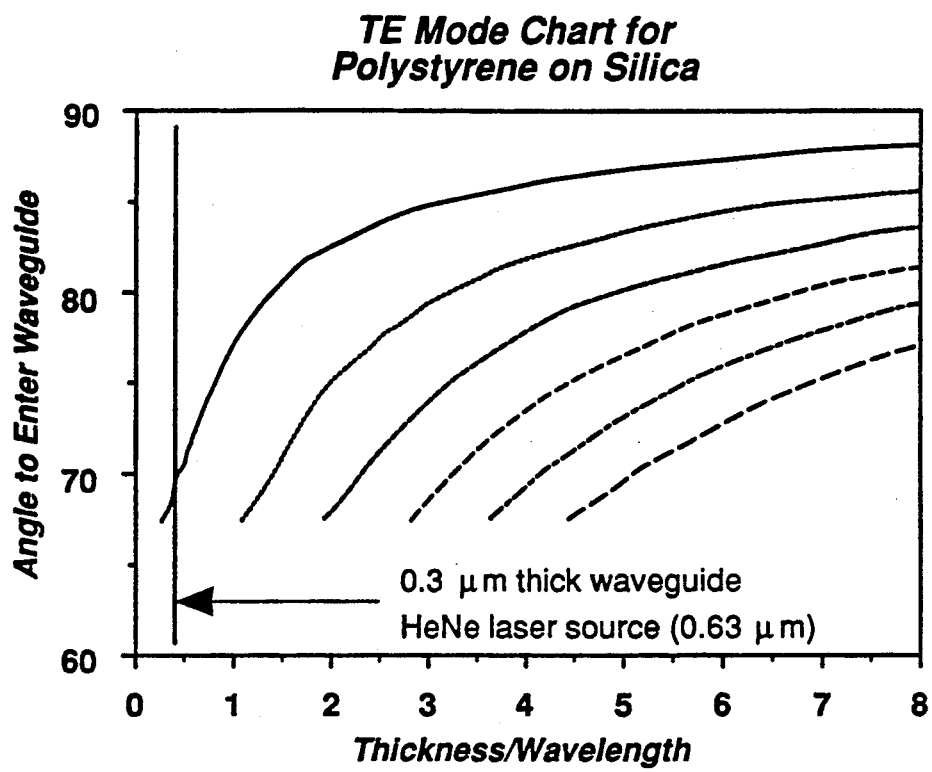
FIG. 3 is a mode chart for a polystyrene waveguide (n2=1.59) on a fused silica substrate, having a refractive index of 1.46, with air above the waveguide ($n_1 = 1.00$).

When the waveguide is physically altered by the presence of the particular chemical species, such as a polystyrene waveguide in the presence of acetone, the angle required to couple into a particular mode changes. A monochromatic light source (HeNe laser at 0.63 μm) was used. FIG. 3 is a mode chart for this waveguide. Each curve in FIG. 3 represents a different mode, or angle, at which light is propagated through the polystyrene waveguide. The calculations are for TE (transverse electric) modes, which represent a particular polarization of light as it enters the waveguide. In FIG. 3, the horizontal axis is the thickness of the waveguide divided by the wavelength of light. The vertical axis is the angle relative to the waveguide normal at which light will propagate in the waveguide in that mode. Thus, the data in FIG. 3 show that the thicker the waveguide, the more modes. For a thick film containing multiple modes, each mode will be entered at a unique angle at a particular wavelength.

FIG. 3 shows the basis of a chemical sensor using a polymer waveguide. The polymer waveguide is polystyrene (having a refractive index of 1.58) on a fused silica substrate having a refractive index of 1.46. Each line is a mode propagated throughout the waveguide (planar configuration). FIG. 3 shows that the angle required to couple light into each mode is dependent upon the wavelength of light and the thickness of the waveguide. The vertical line in FIG. 3 represents a 0.3 μm thick polystyrene waveguide at a wavelength of 0.63 μm corresponding to a HeNe laser. Under these conditions, only one mode is available because the vertical line intersects only one mode curve in FIG. 3. This mode will propagate at an angle to the waveguide of about 69.5°.

If the angle of laser light is fixed at 69.5°, such as in Example 3, eventually coupling of the light into the waveguide will be eliminated as the waveguide is permeated by the vapor. For example, if the thickness increased, the vertical line would move to the right, requiring an angle of greater than 69.5° to propagate in the waveguide. This forms the basis for a remote vapor alarm or chemical sensor with a monochromatic electromagnetic radiation source. This chemical sensor can be as simple as a light-emitting diode or a laser with a relatively inexpensive detector or sensing device, such as a photocell and resistance meter. The photocell can be connected to a simple analog trip-point detection circuit. Several devices can be connected with optical fibers along a process stream or chemical pipeline in an effort to detect leaks of organic solvents or vapors.

A chemical sensor, according to the present invention, was manufactured having a fused silica substrate and a a silicone waveguide spin-coated at a 0.8 μm thickness. The incoupling and outcoupling gratings were etched onto the substrate with 0.5 μm spacings. The distance between the gratings was 1 cm apart. The waveguide refractive index was 1.485 and the substrate 1.46. This sensor can detect pentane vapor.

The signal intensity of a HeNe laser was measured in FIG. 4. When pentane vapor was concentrated over the first surface of the waveguide to change its physical properties, the recorded signal intensity dropped as shown in FIG. 4. Four different pentane vapor concentrations were used (each concentration was applied three times). Each subsequent concentration was 50% of the previous concentration. The amount of signal attenuation was proportional to the pentane vapor concentration, as shown in FIG. 4. These results show that this configuration functioned as a chemical sensor or vapor alarm to determine the presence and concentration of pentane at the first surface of the waveguide.

The specificity of the chemical sensor will depend upon the specificity of the material of the waveguide to a particular chemical species in a mixture. It is important that the material of the waveguide be carefully selected to react with either a particular chemical species, such as a solvent, or a particular class of chemical species to best quantitatively analyze the composition of a mixture in the reaction volume.

The present invention further includes an array of waveguides, such as those illustrated in FIG. 5. There can be one substrate or several substrates. Each waveguide must cover an associated pair of gratings to permit covering of the electromagnetic light source and detector. A monochromatic light source (10), such as a laser, can be directed into a plurality of different waveguide materials. The light signal attenuation can then be monitored at a plurality of detectors each communicating, through the outcoupling grating, with a specific waveguide. Each particular waveguide will react with a particular solvent or class of solvents (e.g., ketones, alcohols). Thus, one can calculate the presence and concentration of several analytes in a mixture using statistical procedures and mathematical models, such as partial least squares.

The following examples are designed to illustrate several aspects of the present invention and should not be construed to interpret the scope of the invention.

EXAMPLE 1

This example illustrates the fabrication of a grating pair. Grating pairs were fabricated on the surface of microscope slides (VWR Catalog #48300-025) that were scribed with a diamond pen and broken give to give final dimensions of 37×25 mm. The slides were cleaned in a solution of sulfuric acid and hydrogen peroxide (7:3), rinsed with deionized water, and quickly dried with argon. The clean slides were placed in a quartz tube, sealed, and heated at 400° C. at 40 mTorr for one hour. A liquid nitrogen cold trap was used between the horizontal tube furnace and the rotary vane pump. After the furnace was allowed to cool to 100° C., a valve was opened and 2 ml of hexamethyldisilazane (HMDS, Baker) was allowed to vaporize and react with the slides. HMDS reacts with surface hydroxyl groups to produce a hydrophobic surface for the application of a photoresist. The contact angle was measured to be 75° on a Reme Hart contact angle apparatus after the HMDS reaction. About 0.35 μm of photoresist (Hoechst-Celanese AZ1350-SBF) was applied to the surface of the substrate using a spin coater (Headway EC101) at 7,000 rpm for 30 minutes. An interferometric method was used to directly expose the image of the linear grating in the photoresist coating based upon Lloyd's mirror fringes.

The gratings were produced by a krypton laser at a wavelength of 406 nm. A beam expander produced a 1-cm diameter beam that was focused so that half fell upon a mirror in contact with the substrate, and the other half was directly incident upon the substrate. The Lloyd's mirror fringes were produced at the substrate by interference between the beam reflected from the mirror and the beam that was directly imaged on the substrate. The period of the fringes (d), and hence the grating, is given by the following equation:

$d = \lambda/(2\sin Z)$ where Z is the angle of incidence of the laser beam relative to the mirror. An angle of 30.4° was used to obtain the 0.4-μm gratings with a laser wavelength of 0.406 μm.

An incident laser power density of 1 mW/cm² was used with an exposure time for the photoresist of 30 seconds. The exposed photoresist was developed for 20 seconds in a diluted developer (1 part Hoechst-Celanese AZ351 developer:7 parts deionized water). After developing, a diluted, wet etching solution (1 part Transeme-buffered HF:10 parts deionized water) was used to transfer the photoresist grating pattern to the substrate. Reaction with this solution for 15 seconds produced gratings with 0.4 μm spacing and a depth of about 0.1 μm, as measured on a fractured sample with a scanning electron microscope (SEM). The vertical shape of the grating was approximately rectangular, with only minimal undercutting, or widening at the bottom. The photoresist was removed with acetone and the substrate was cleaned in the sulfuric/peroxide solution described above prior to adding the waveguide.

EXAMPLE 2

This example illustrates the fabrication of waveguides on the substrates containing the gratings that were made in Example 1. A polymeric waveguide was made from polystyrene. Polystyrene (Polysciences #3433, 30 K MW) was dissolved in methyl isobutyl ketone (MIBK) as a 10% solution by weight. The solution was applied to the clean substrate containing the pair of etched gratings by spin-coating at 2,000 rpm. After heating 60° C. for one hour, the thickness of the waveguide was calculated to be about 0.4 μm by analyzing the fringe pattern in the transmission spectrum taken normal to the waveguide using a Hewlett-Packard 4851 photodiode array spectrometer.

Tantalum pentoxide (Ta$_2$O$_5$) waveguides were fabricated in an MRC rf-diode, gas-reactive, sputtering system with a Ta metal target. The sputtering target had a power density of 1.5 W/cm². The samples were placed on a water-cooled copper stage. Constant gas pressures were used for the Ar-O$_2$ mixtures during each experiment. The total gas pressure was 5–8 mTorr with 5%–15% oxygen in the mixture. The sputtering rate of Ta$_2$O$_5$ on the substrate under these conditions was 2–4 nm/min, dependent upon the total pressure.

EXAMPLE 3

This example illustrates the testing of an integrated spectrometer using the substrate, gratings, and waveguides described in Examples 1 and 2. The propagation loss of electromagnetic radiation through the waveguides was measured using a 2×2 mm coherent optical fiber bundle attached to a silicon detector and a movable plate support driven by a linear stepper driver. The light (electromagnetic radiation) source was a HeNe laser at a wavelength of 0.632 μm. The light was coupled into the waveguide by the grating described in Example 1. The image of a thin streak of scattered light emanating from the propagated beam in the waveguide was visibly centered in the coherent optical fiber bundle. The strip chart recording from the silicon detector was digitized to determine the propagation loss. The tantalum pentoxide waveguide had a propagation loss of 8.6 dB/cm, as determined from a least-squares regression analysis of the data. This loss indicates that about 14% of the initial light intensity measured is detected from the propagated beam 1 cm away.

EXAMPLE 4

An integrated spectrometer was constructed using the tantalum pentoxide waveguide of Example 2 and the substrate and gratings constructed in Example 1. An argon ion laser (Spectra Physics 156) was used as a light source. The argon ion laser was operated sequentially by tuning through several lines in order to determine the relation between the coupling angle and the incident wavelength. The laser was also operated in a multiline configuration in order to measure the intensity and spatial dispersion of the lines simultaneously at the photodiode detector array. The laser was focused into a 200-μm diameter, high-numerical aperture fiber (Ensign Bickford), which was, in turn, focused onto a high-numerical aperture (N.A. 0.6), 0.29 pitch, gradient index lens (NSG America SELFOC SLH-1.8 mm-0.29 P-NC-0.63 μm). The convergent beam from this lens was focused onto the incoupling grating through the substrate (1 mm thick).

A second grating coupled to the light of the waveguide for detection by the self-scanning photodiode array detector (EG&G Reticon S Series). The center-to-center spacing of the elements in this photodiode array is 25 μm and the height of each element is 2.5 mm. The output of the photodiode array was sampled at 50 kHz by an analog-to-digital converter (Metrabyte-16) connected to a computer (IBM PC-XT).

A complete scan of the photodiode array took about 20 ms at that frequency.

FIG. 6 shows the spectrum of light directed at the incoupling grating at all angles produced by the gradient refractive index lens. FIG. 7 shows the resulting output of the linear array detector. The outcoupling grating dispersed each wavelength at a unique angle. Thus the different argon laser lines had been dispersed to different positions on the photodiode array detector, as shown in FIG. 7. These data demonstrate the principle of multiple wavelength light into the waveguide and spatially dispersed wavelength light out of the waveguide.

EXAMPLE 5

This example illustrates a chemical sensor that is able to detect the concentration of the chemical species, pentane. A chemical sensor was constructed according to the inventive design. The waveguide was made from silicone rubber (Petrarch PS-254) at a thickness of 0.8 μm as spin-coated on a fused silica substrate containing uniform entrance and exit gratings of 0.5-μm spacings. The gratings were placed 1 cm apart. The refractive index of the waveguide was calculated to be approximately 1.485. The refractive index of the fused silica was 1.460 and the light source was a HeNe laser (0.632 μm).

The chemical sensor was exposed to pentane vapor at the first surface of the waveguide. A stream of nitrogen gas was flowing at 31 ml/min over the waveguide surface. At various intervals, an injection of pentane vapor at 25° C. was injected into the nitrogen stream by a LLC injection valve (0.2 ml of vapor). The first group of triplicate injections was saturated pentane vapor where pentane was equilibrated with air at room temperature. Subsequent concentrations were a series of 50% dilutions.

Light was coupled into the waveguide at a fixed angle at a fixed angle and detected at a fixed angle by a silicon photodiode. FIG. 4 shows the drop in intensity seen by the diode in response to the injection of pentane vapor. Data were collected every 200 milliseconds. FIG. 4 shows significant dropping in intensity following each pentane vapor injection. Accordingly, the chemical sensor was able to detect pentane vapor by indicating a drop in signal intensity.

EXAMPLE 6

This example illustrates the construction of a noninteractive waveguide for visible light range detection of an analyte or analytes in a reaction volume. The spectrometer is constructed with holographically ruled lines in a photoresist for a grating on a fused silica substrate and wet chemically etched. A noninteractive waveguide composed of $SiO_2$-$TiO_2$ with a refractive index of 1.8 to 1.9 is added to the substrate. The waveguide and substrate are heated to collapse the pore structure of the waveguide and to fill in the grating grooves. The waveguide is determined to be 0.25 $\mu$m thick. The grating has 0.5-$\mu$m spacing and depth. The grating is formed as a "slow chirp" to 0.48- to 0.52-$\mu$m spacings. A collimated white light source transmits electromagnetic radiation to the grating via a fiber optic and a GRIN (gradient refractive index) lens. The outcoupling grating is chirped in an identical manner as the incoupling grating. The spectrometer uses an array detector located approximately coplanar to the propagation direction.

EXAMPLE 7

This example illustrates the construction of a chemical sensor using an interactive waveguide. The chemical sensor is sensitive to water (i.e., humidity). The substrate is fused silica containing an incoupling and outcoupling grating of 0.5-$\mu$m depth and spacing. The waveguide is made of polyamide of approximately 0.5-$\mu$m thickness. The light source is a single-wavelength, 670-nm laser diode and the detector is an apertured photodiode.

From the foregoing, it will be appreciated that, although specific embodiments of the invention have been described herein for purposes of illustration, various modifications may be made without deviating from the spirit and scope of the invention.

What is claimed is:

1. An integrated spectrometer for chemical analysis by evanescent electromagnetic radiation absorption in a reaction volume, comprising:

a noninteractive sample waveguide having a uniform thickness and having a first surface and a second surface, and having an electromagnetic radiation entrance end and exit end, wherein the first surface communicates with the reaction volume along the region between the entrance end and exit end of the sample waveguide;

a substrate having a top surface and a bottom surface and comprising a material characterized by allowing for the transmission of electromagnetic radiation, an entrance grating and an exit grating etched or deposited on the top surface of the substrate, such that the entrance grating communicates with the entrance end and the second surface of the waveguide and couples electromagnetic radiation into the waveguide, and the exit grating communicates with the exit end and the second surface of the waveguide and couples electromagnetic radiation out of the waveguide, wherein the gratings comprise parallel spacings and wherein the refractive index of the substrate is different from the refractive index of the waveguide;

an electromagnetic radiation source directed toward the entrance grating; and an electromagnetic radiation sensing device directed toward the exit grating.

2. The integratred spectrometer of claim 1, further comprising a thin polymeric overcoat layer communicating with the first surface of the waveguide, wherein the overcoat layer is thinner than the waveguide and wherein the polymeric overcoat permits evanescent interaction of the electromagnetic radiation with the reaction volume.

3. The integrated spectrometer of claim 2 wherein the polymeric overcoat layer is no thicker than 0.01 $\mu$m.

4. The integrated spectrometer of claim 1, further comprising a thick overcoat layer communication with the first surface of the waveguide and placed over the entrance grating and exit grating, the overcoat layer serving to prevent interaction between the waveguide and the reaction volume in the region of the entrance and exit gratings.

5. The integrated spectrometer of claim 1, further comprising a second waveguide acting as a reference waveguide having a thick overcoat layer over the first surface of the reference waveguide at least in the region between the gratings and being characterized by preventing evanescent interaction of the electromagnetic radiation with the reaction volume, wherein the sample waveguide and the reference waveguide may be communicating with the same substrate or separate substrates.

6. The integrated spectrometer of claim 5 wherein the reference waveguide and the sample waveguide each have separate electromagnetic radiation sources, sensing devices, incoupling gratings, and outcoupling gratings.

7. The integrated spectrometer of claim 5 wherein the reference waveguide and the sample waveguide use the same electromagnetic radiation source bifurcated to direct equivalent electromagnetic radiation to each waveguide.

8. The integrated spectrometer of claim 1, further comprising a polymeric overcoat layer communicating with the first surface of the waveguide, wherein the overcoat layer contains an indicator system that changes its absorption characteristics as a function of an interaction with the reaction volume.

9. The integrated spectrometer of claim 1 wherein the entrance and exit gratings are selected from the group consisting of etched gratings in the top surface of the substrate, ruled gratings in the top surface of the substrate, holographically manufactured gratings, metal gratings, chirped gratings, curved gratings, and combinations thereof.

10. The integrated spectrometer of claim 9 wherein the metal gratings comprise metal lines separated by bare substrate.

11. The integrated spectrometer of claim 1 wherein the noninteractive waveguide material is selected from the group consisting of glass, metal oxides, $Ta_2O_5$, $ZrO_2$, $Al_2O_3$, nitrides, fused silica, Si, Ge, zinc selenide, noninteractive polymers, and combinations thereof.

12. The integrated spectrometer of claim 1 wherein the electromagnetic radiation source comprises a plurality of wavelengths and are within the range of ultraviolet light to infrared light.

13. The integrated spectrometer of claim 12 wherein the electromagnetic radiation source is within the range of near-infrared light to infrared light.

14. The integrated spectrometer of claim 1 wherein the electromagnetic radiation source is a collimated visible light source.

15. The integrated spectrometer of claim 1 wherein the spectrometer further comprises fiber optics to transport the electromagnetic radiation between the source and the entrance grating and/or between the exit grating and the sensing device.

16. A method for continuously measuring the concentration of an analyte or analytes in a reaction volume, comprising:
    contacting a first surface of a noninteractive waveguide having a uniform thickness with the reaction volume, wherein the waveguide further comprises a second surface communicating with an analysis device, wherein the analysis device comprises a) a substrate having a top surface communicating with the second surface of the waveguide and a bottom surface and further comprising a material that allows for the transmission of electromagnetic radiation, b) entrance and exit gratings etched or deposited on the top surface of the substrate such that the entrance grating couples electromagnetic radiation into the waveguide and the exit grating couples electromagnetic radiation out of the waveguide, c) an electromagnetic radiation source directed toward the entrance grating, and d) an electromagnetic radiation sensing device directed toward the exit grating;
    directing electromagnetic radiation to propagate through the waveguide such that the interaction of the analyte or analytes along the first surface of the waveguide in the region between the entrance and exit gratings modulates an evanescent wave; and
    detecting the characteristics of electromagnetic radiation by the electromagnetic radiation sensing device.

17. A chemical sensor to determine the presence and concentration of a particular chemical species in a chemical composition, comprising:
    an interactive waveguide having a uniform thickness, a first surface, a second surface, and an electromagnetic radiation entrance end and exit end, wherein the first surface communicates with the chemical composition and wherein the waveguide is capable of a physical change in the refractive index or thickness, or both, of the waveguide when the first surface communicates with the chemical composition containing the particular chemical species along the region between the entrance end and exit end of the waveguide;
    a substrate having a top surface and a bottom surface and comprising a material of a different refractive index of the waveguide and allowing for the transmission of the appropriate wavelength of electromagnetic radiation, wherein the top surface of the substrate supports the second surface of the waveguide and communicates with the waveguide;
    an entrance grating and an exit grating, wherein the entrance grating couples electromagnetic radiation into the entrance end of the waveguide and the exit grating couples electromagnetic radiation out of the exit end of the waveguide;
    an electromagnetic radiation source directed toward the entrance grating; and
    an electromagnetic radiation sensing device directed toward the exit grating.

18. The chemical sensor of claim 17 wherein the particular chemical species is a solvent or a vapor characterized by the ability to alter the physical characteristics of the interactive waveguide.

19. The chemical sensor of claim 17 wherein the entrance and exit gratings are selected from the group consisting of etched gratings in the top surface of the substrate, ruled gratings in the top surface of the substrate, metal gratings, chirped gratings, curved gratings, and combinations thereof.

20. The chemical sensor of claim 19 wherein the metal gratings comprise metal lines separated by bare top surface of substrate.

21. The chemical sensor of claim 17 wherein the interactive waveguide material is a polymer selected from the group consisting of polystyrene, cellulose acetate, polyvinyl chloride, polyvinyl alcohol, polyphosphazines, silicones, polybenzenes, polyimides, vinyltrimethyl siloxanes, and combinations thereof.

22. The chemical sensor of claim 17 wherein the electromagnetic radiation source is a monochromatic source and is within the range of ultraviolet to near infrared.

23. The chemical sensor of claim 21 wherein the electromagnetic radiation source is a monochromatic laser.

24. The chemical sensor of claim 17 wherein the chemical sensor further comprises fiber optics to transport electromagnetic radiation between the source and the entrance grating and/or between the exit grating and the sensing device.

25. The chemical sensor of claim 17, further comprising a thick overcoat layer communication with the first surface of the waveguide and placed over the entrance grating and exit grating, such overcoat layer serving to prevent interaction between the waveguide and the reaction volume in the region of the entrance and exit gratings.

26. A method for monitoring for the presence and concentration of a particular chemical species in a chemical mixture contained in a reaction volume, comprising:
    contacting a first surface of an interactive waveguide having a uniform thickness with the reaction volume, wherein the waveguide further comprises a second surface communicating with an analysis device, wherein the analysis device comprises a) a substrate having a top surface communicating with the second surface of the waveguide and a bottom surface and further comprising a material that allows for the transmission of electromagnetic radiation, b) entrance and exit gratings etched or deposited on the top surface of the substrate such that the entrance grating couples electromagnetic radiation into the waveguide and the exit grating couples electromagnetic radiation out of the waveguide, c) an electromagnetic radiation source directed toward the entrance grating, and d) an electromagnetic radiation sensing device directed toward the exit grating;

directing electromagnetic radiation to propagate through the waveguide such that the interaction of the chemical species with the interactive waveguide in the region between the entrance and exit gratings will change the physical character of the waveguide to affect the electromagnetic radiation propagation through the waveguide; and detecting electromagnetic radiation leaving the exit grating by the electromagnetic radiation sensing device.

27. The method of claim 26, wherein the electromagnetic radiation is monochromatic at a wavelength in the ultraviolet to infrared range.

* * * * *

UNITED STATES PATENT AND TRADEMARK OFFICE
CERTIFICATE OF CORRECTION

PATENT NO. : 5,082,629

DATED : January 21, 1992

INVENTOR(S) : Lloyd W. Burgess, Jr.; Don S. Goldman

It is certified that error appears in the above-identified patent and that said Letters Patent is hereby corrected as shown below:

On the cover page, change the first named assignee from "The Board of the University of Washington" to -- The Board of Regents of the University of Washington --.

Col. 1, line 3, immediately before "Technical Field", insert -- This invention was made with government support under grant number DE-AC06-76RLO 1830 awarded by the Department of Energy. The government has certain rights in the invention.--.

Signed and Sealed this

Twenty-second Day of June, 1993

Attest:

MICHAEL K. KIRK

*Attesting Officer*  *Acting Commissioner of Patents and Trademarks*